United States Patent
Del Rio et al.

(10) Patent No.: US 9,295,478 B2
(45) Date of Patent: *Mar. 29, 2016

(54) SURGICAL FILE

(71) Applicant: DEPUY SYNTHES PRODUCTS, LLC, Raynham, MA (US)

(72) Inventors: Eddy H. Del Rio, Royal Palm Beach, FL (US); David Narducci, Lake Worth, FL (US); Michael Menard, Boynton Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 208 days.

This patent is subject to a terminal disclaimer.

(21) Appl. No.: 13/897,864

(22) Filed: May 20, 2013

(65) Prior Publication Data

US 2013/0338670 A1 Dec. 19, 2013

Related U.S. Application Data

(63) Continuation of application No. 12/586,092, filed on Sep. 17, 2009, now Pat. No. 8,444,648.

(51) Int. Cl.
*A61B 17/00* (2006.01)
*A61B 17/16* (2006.01)

(52) U.S. Cl.
CPC ......... *A61B 17/1659* (2013.01); *A61B 17/1624* (2013.01); *A61B 17/1628* (2013.01)

(58) Field of Classification Search
CPC ........... A61B 17/1604; A61B 17/1608; A61B 17/1659
See application file for complete search history.

(56) References Cited

U.S. PATENT DOCUMENTS

| | | | |
|---|---|---|---|
| 5,571,130 A | 11/1996 | Simpson | |
| 7,390,330 B2 | 6/2008 | Harp | |
| 7,666,186 B2 * | 2/2010 | Harp | ............................... 606/85 |
| 2003/0083681 A1 | 5/2003 | Moutafis | |
| 2006/0129159 A1 | 6/2006 | Lee | |
| 2006/0129160 A1 | 6/2006 | Liu et al. | |
| 2006/0206117 A1 | 9/2006 | Harp | |
| 2009/0114181 A1 | 5/2009 | Okabe | |
| 2011/0066154 A1 | 3/2011 | Narducci et al. | |

FOREIGN PATENT DOCUMENTS

| | | |
|---|---|---|
| JP | 60-142842 | 7/1985 |
| JP | 2006-500998 | 1/2006 |

OTHER PUBLICATIONS

Extended European Search Report dated Oct. 8, 2014, in connection with International Application No. PCT/US2010/002540.
International Preliminary Report on Patentability and Written Opinion, dated Mar. 20, 2012, in connection with International Application No. PCT/US2010/002540.
International Search Report, dated Nov. 5, 2010, in connection with International Application No. PCT/US2010/002540.

* cited by examiner

*Primary Examiner* — Nicholas Woodall
(74) *Attorney, Agent, or Firm* — Meunier Carlin & Curfman LLC

(57) ABSTRACT

A surgical file instrument including a surgical file assembly having an elongated tubular member with a guide/shield supporting the blade of the surgical file and being formed on the distal end thereof, the guide/shield portion being generally planar shaped and having an elongated longitudinally extending dimple defining a rail for guiding said blade and keeping it central and preventing wobbling. The side edges of said guide/shield extend upwardly and bear against the underside of the blade for supporting the same.

19 Claims, 5 Drawing Sheets

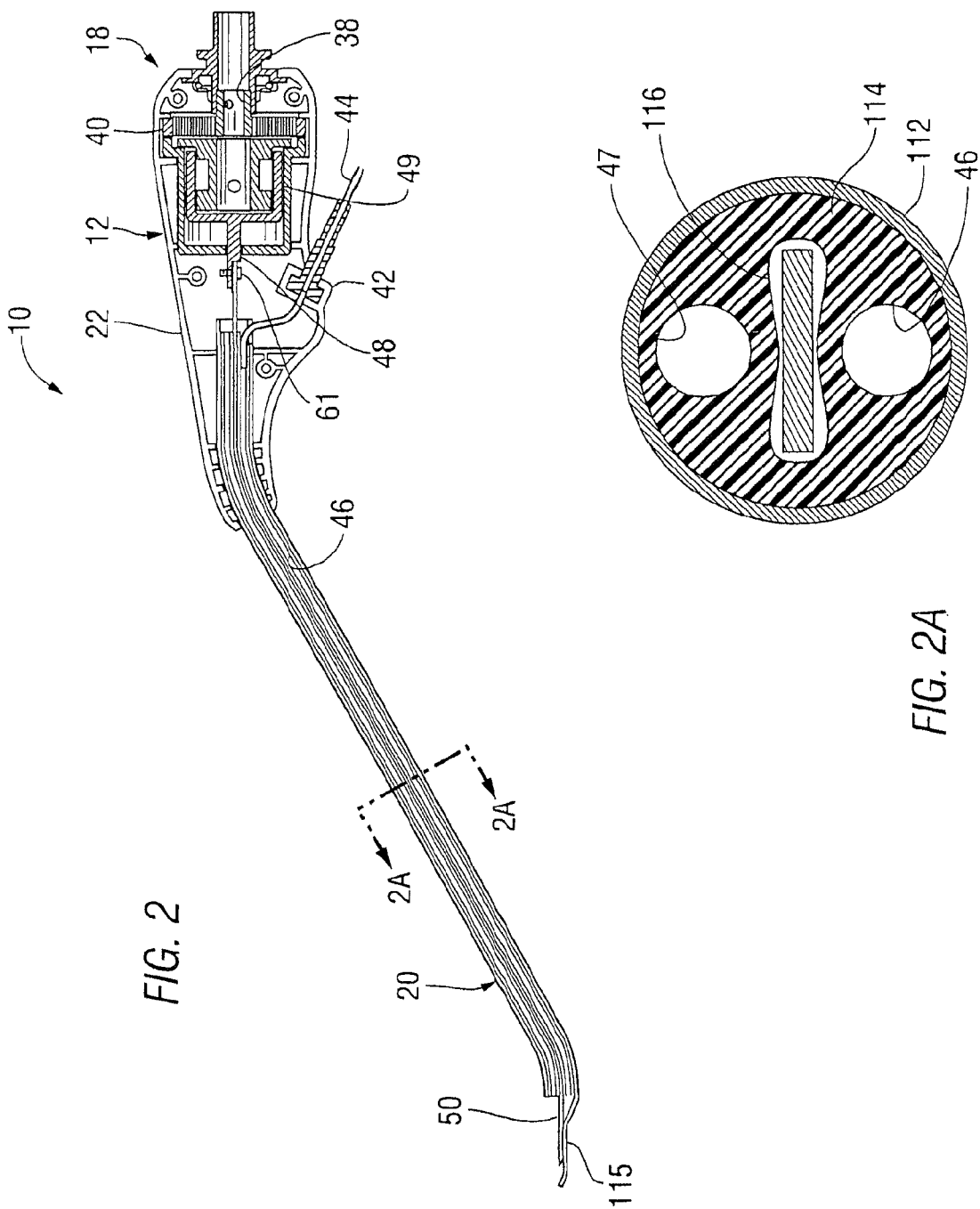

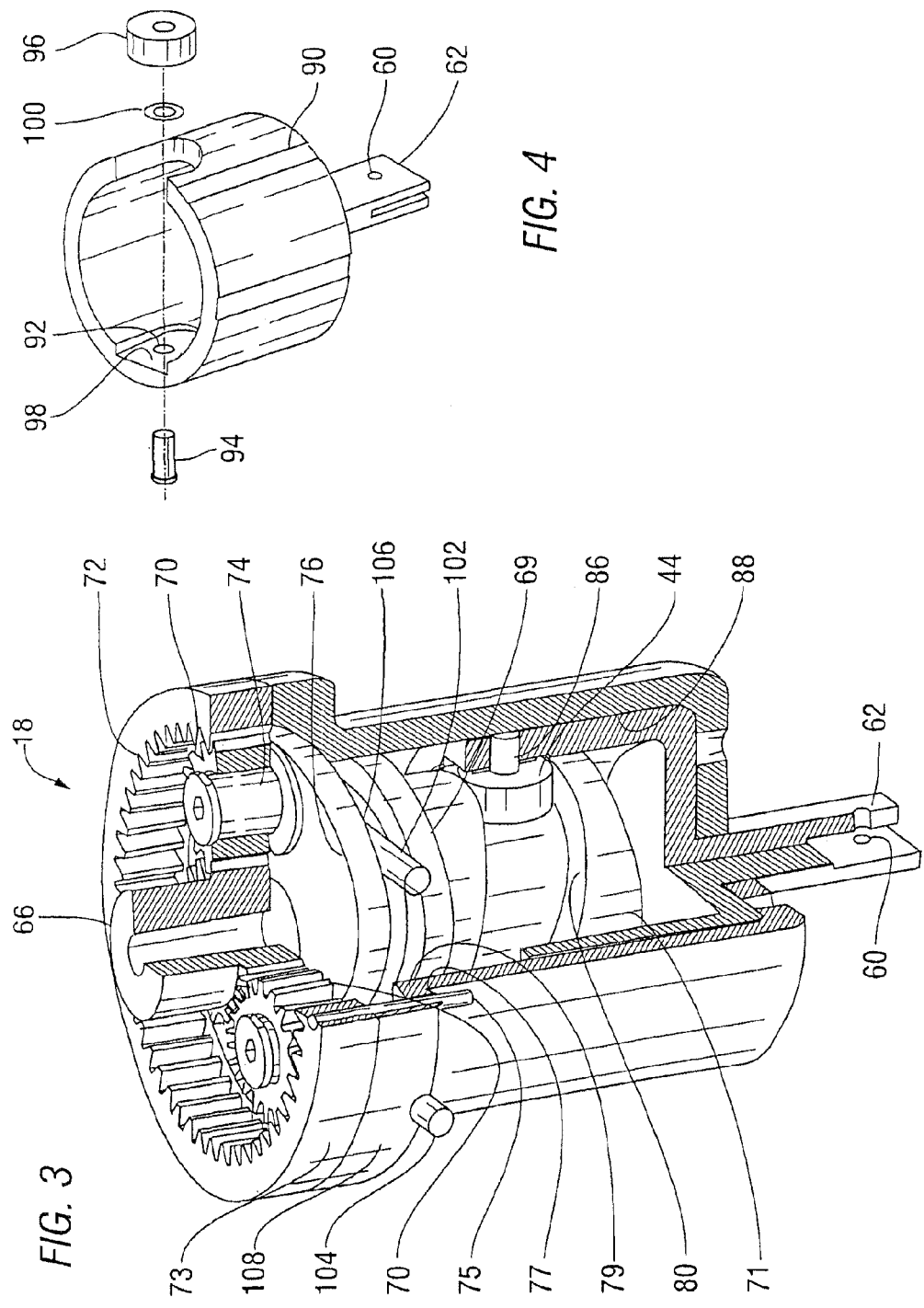

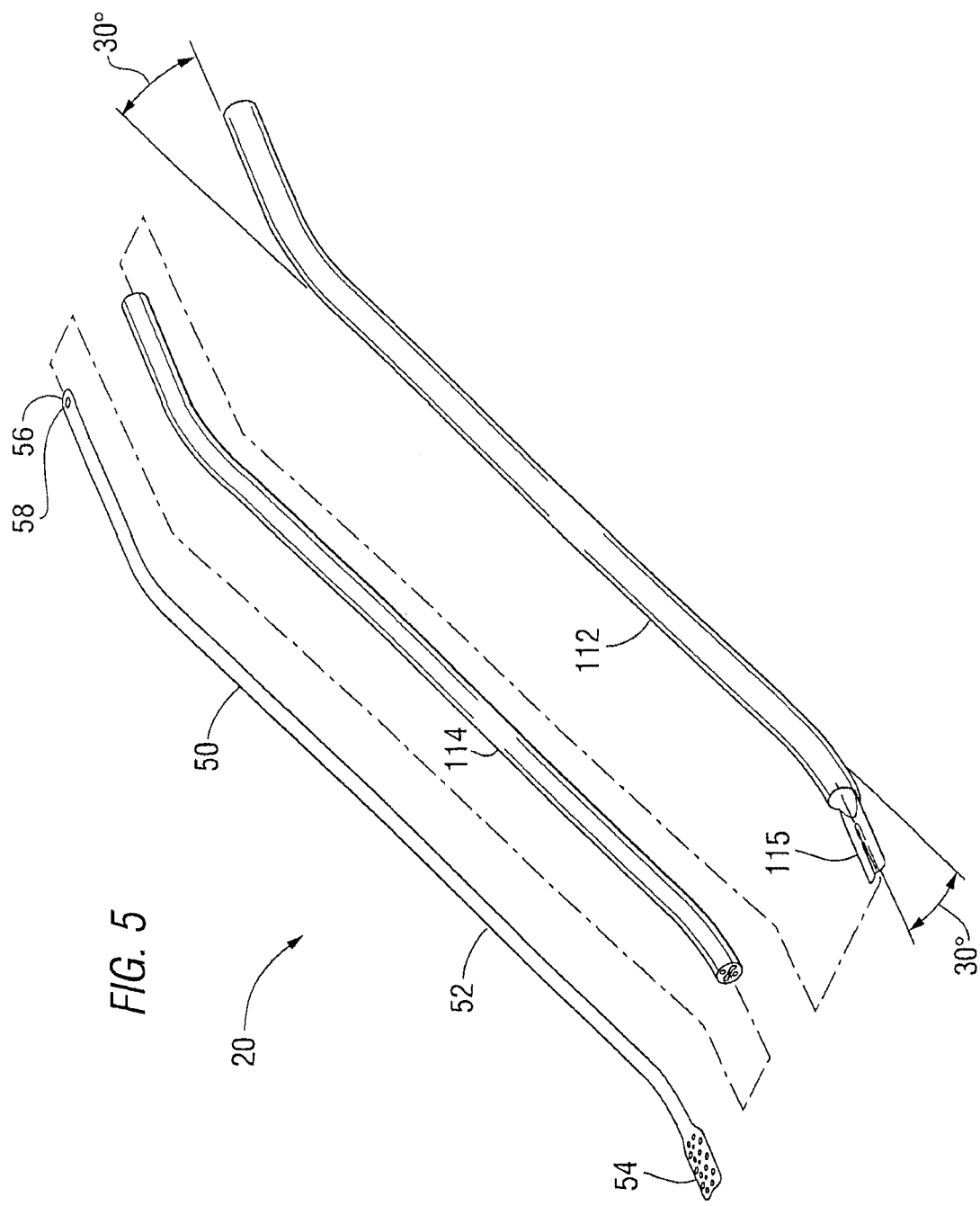

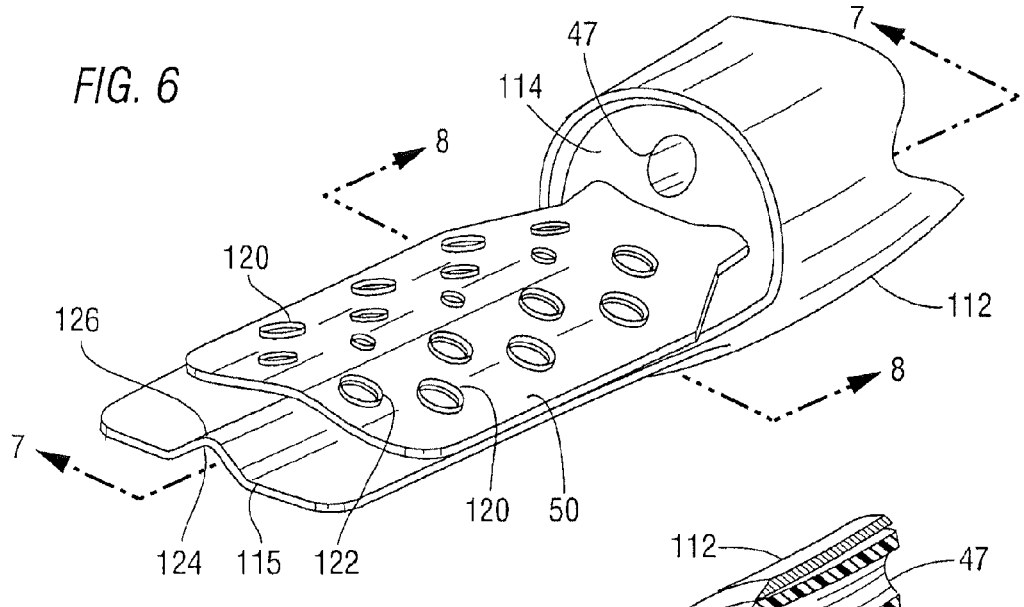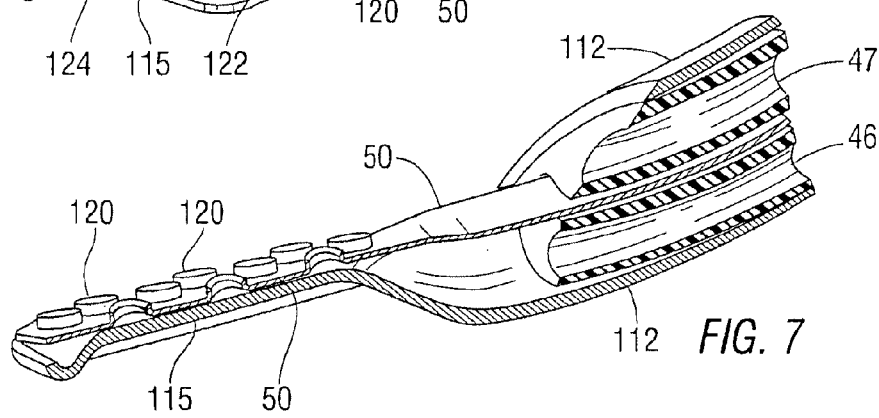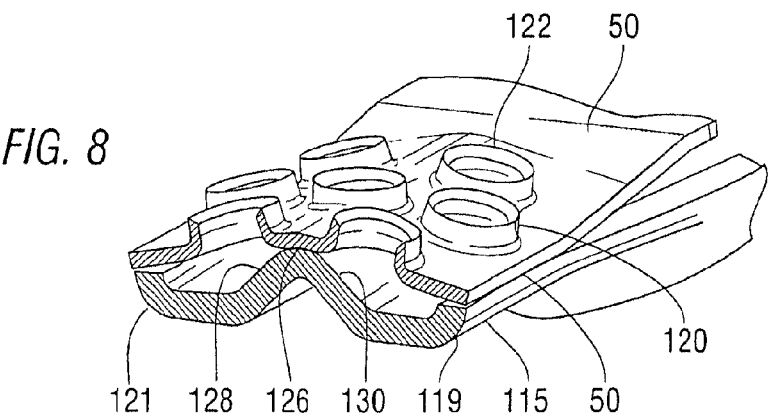

SURGICAL FILE

RELATED APPLICATIONS

This application is a continuation application of U.S. application Ser. No. 12/586,092, filed Sep. 17, 2009, entitled "SURGICAL FILE" which is related to U.S. Pat. No. 8,388,622 filed Sep. 17, 2009, entitled "SURGICAL FILE INSTRUMENT CONSTRUCTION WITH MECHANISM TO CONVERT ROTARY MOTION TO RECIPROCAL MOTION," both invented by David Narducci, Stephen Bucina, Michael Menard and Eddy Del Rio, the entire disclosures of which are hereby incorporated by reference.

BACKGROUND OF THE INVENTION

1. Field of the Invention

This invention relates to a surgical file instrument that is used in a surgical procedure for removing bone from a patient. More particularly, the invention relates to the file and guide/shield portion for cutting, removing, grinding, shaping and sculpturing bone and to the configuration of the file, and guide/shield to assure that the reciprocating file remains centered when being used and precludes any wobbling motion.

2. Description of Related Art

There are a number of surgical file instruments that are commercially available and as one skilled in this art appreciates, it is abundantly important that the blade of the file of the surgical file instrument when in operation remains centered and does not vacillate from that plane. In other words, the file must remain within its operating plane and stay along the center line for precision bone removal. Moreover, the file blade must be shielded so that the portion of the anatomy that isn't being worked on is not inadvertently cut or bruised. The file must be dimensioned so that it can be used in very tight and close areas in the body that are typically difficult to get to in order to perform precision surgical operations.

There are commercially available surgical file instruments that have a sundry of applications that may be used by a surgeon for the treatment of certain types of pathology. For example, U.S. Pat. No. 7,390,330 ('330) granted to Harp on Jun. 24, 2008 essentially relates to a surgical file instrument that is similar to the surgical file instrument described in the present patent application, however, the invention described in this patent application patentably distinguishes over the surgical file disclosed in the U.S. Pat. No. 7,390,330 ('330), supra. The '330 patent, supra, discloses a shielded reciprocating surgical file system and allows a user to navigate the file into hard to access parts of the patient's body. It also describes a transmission mechanism that converts rotary motion from a motor into reciprocating motion, pump mechanism and an irrigation system that supplies fluid to the surgical site.

In one embodiment in the '330 patent, for example, the cutting blade is shielded on five sides to provide a shielded surgical file. The file can be dimensioned so that it extends generally straight, curved, angled or bent along the longitudinal axis. The file needs to be compatible to fit into the human or mammalian anatomy portions. Its thickness must be thin so that it fits into small spaces such as between a nerve and the foramen opening that it is passing through and the cutting blade can be shaped or contoured. The present invention is capable of performing these types of operation with a less complicated file. In other words, the present invention is characterized as being relatively simple to, make, less costly and yet, it is efficacious.

To obtain the reciprocal motion from the rotary motion, the structure disclosed in the '330 patent, supra, utilizes a torus transmission device which may include an integral shaft or a rigidly connected shaft. The torus drive and drive shaft are rotatable about a central rotation axis and has a generally circular or curvilinear cam portion with the torus central axes being at an offset angle. The variable thickness of the torus cam surface produces a hybrid dual or twin torus. Similar to what is disclosed in the '330 patent, supra, the present invention has utility for many medical procedures that are typically the concern in neurosurgery, orthopedic surgery and plastic surgery, amongst others. For example in neurosurgery, the neruroforamen may need enlargement and the file can be instrumental in removing rigid bony vertebral structure to allow the nerve roots to pass there through. In orthopedic surgery the knee may require sculpturing. And, in plastic surgery bone and tissue sculpturing may be required for nose reshaping and rhinoplasty.

It is imperative in this type of surgical file instrument that the file blade doesn't wobble or get out of line while being used. To this end we have found that by contouring the central portion of the guide/shield with a dimple having an apex bearing against the underside of the blade and providing a unique configuration to the side portions of the dimple extending from the apex in which the file blade is in sliding relationship, the surgical file and blade remain in a fixed plane during its reciprocating condition.

While this invention provides the configuration for assuring that the file remains in-line, this feature is in combination with a surgical file instrument that includes a specific motion converter having a planetary gear system and a cam with a thrust control as well as having a file assembly that includes an elongated outer tube casing, a file having an elongated angular shaft portion having a blade on the distal end and a tang on the proximal end and an encapsulated elongated cylindrical solid tube of plastic material. The solid tube is formed with an elongated generally "infinity symbol" shaped aperture and lumens extending in a longitudinal direction. The "infinity shaped" lumen serves as a passageway for the shaft of the surgical file and the other lumens serve to define passageways to access the surgical site.

SUMMARY OF THE INVENTION

An object of this invention is to provide an improved surgical file.

A feature of this invention is to provide for a surgical file an improved configuration of the shield for the file wherein the central portion thereof is formed with a dimple that is in sliding relationship with the file.

Another feature of this invention is the outer tube casing that fairs into a flattened portion at the distal end that lies in contiguous relation to the file blade and defines a guide and shield therefor.

A feature of this invention is the combination of a motion converter that converts rotary to reciprocal motion, a surgical file assembly that includes a longitudinally extending dimple formed in the guide/shield that is in sliding relationship with the file blade in order to insure that the blade remains in-line during its reciprocating condition. The motion converter includes a planetary gearing system, cam, dome and thrust control and the surgical file assembly includes a longitudinal extending tube case, a longitudinally extending solid insert in said tube case and a longitudinally extending file in said solid insert.

The foregoing and other features of the present invention will become more apparent from the following description and accompanying drawings.

BRIEF DESCRIPTION OF THE DRAWINGS

FIG. 2 is an assembled view in section of the surgical file instrument depicted in FIG. 1;

FIG. 2A is a sectional view taken along lines 2A-2A if FIG. 2;

FIG. 3 is a partial enlarged view in perspective and section illustrating the motion converter of this invention:

FIG. 4 is an enlarged view in perspective of the drum depicted in FIG. 3;

FIG. 5 is an exploded view in elevation illustrating the file assembly of this invention;

FIG. 6 is an enlarged partial view in perspective of the file, the file blade, the file shield and the file assembly;

FIG. 7 is a sectional view taken along lines 7-7 of FIG. 6; and

FIG. 8 is a sectional view taken along lines 8-8 of FIG. 6.

DETAILED DESCRIPTION OF THE INVENTION

Figure 1:
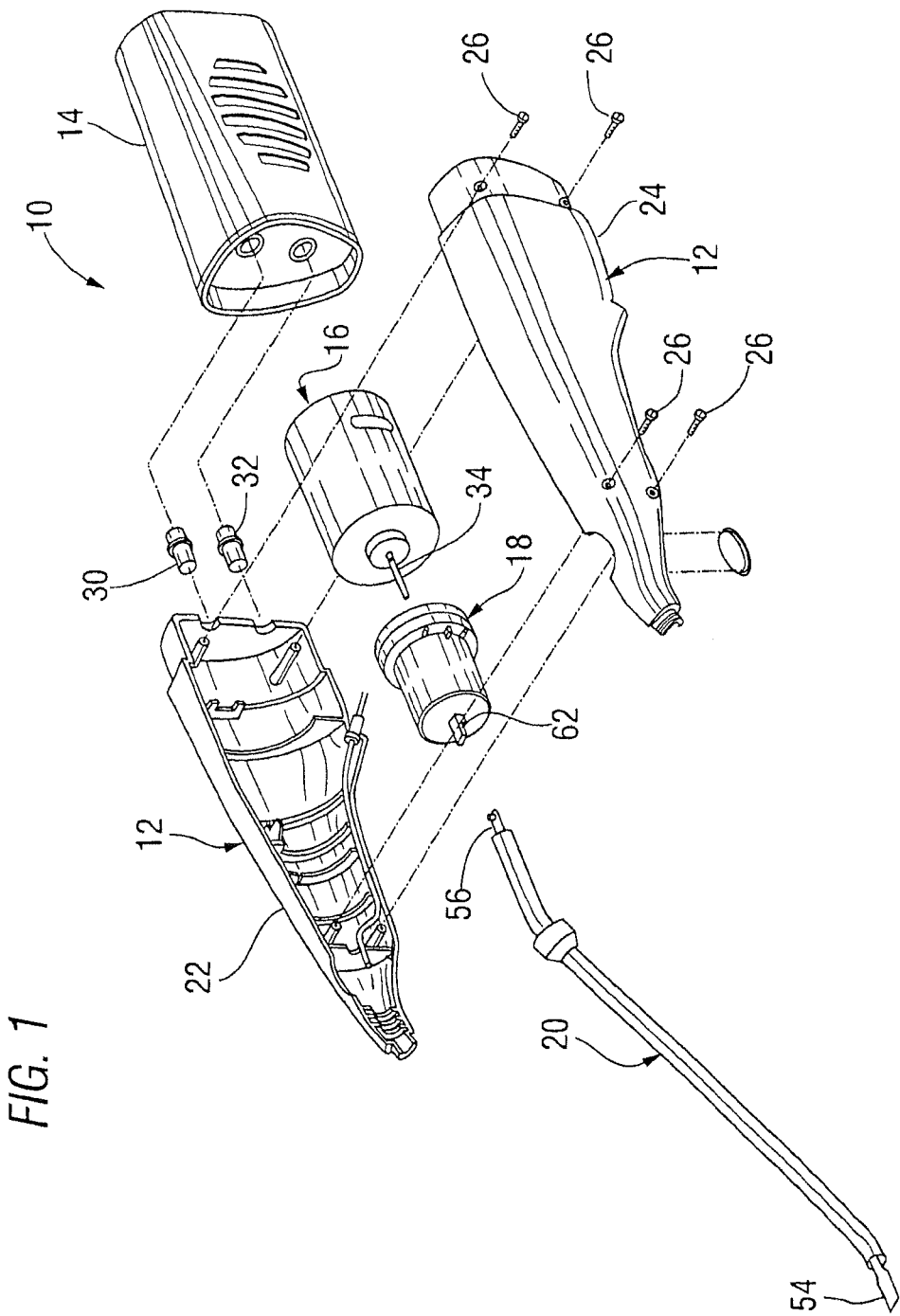
FIG. 1 is an exploded view in perspective illustrating the invention.

As shown in the preferred embodiment of this invention, the configuration of the file assembly wherein the outer tube casing includes a solid plastic tube that describe a particular shape and number of lumens, as will be appreciated by those skilled in this surgical file instrument technology, the shape and numbers of lumen may vary without departing from the scope of this invention. The same is true for the various dimensions and angles of the file assembly which may take the form of non-angularly shaped configurations, and the size including the width and thickness will well depend on the anatomy of the patient being operated on. The types of blades of the file may be different from the one depicted in the preferred embodiment, as for example, it may include abrasive cutting surfaces instead of the micro-holes that are shown in this application.

The invention can best be seen by referring to FIGS. 1-4 which show the surgical file instrument generally illustrated by reference numeral 10 comprising the outer split casing 12, the battery 14, electric motor 16, the motion converter 18, and the file assembly 20. In the assembled condition as seen in FIG. 2, the casing 12 is formed in two generally cylindrical members 22 and 24 that are suitably attached by the screws 26 threadably engaging the threaded lugs 28. The terminals 30 and 32 connect the motor 16 to the battery 14 for powering the motor and driving drive shaft 34. In turn, the drive shaft 32 provides rotary motion to the motion converter 18, as will be described in detail herein below. As noted in FIG. 2, the drive shaft 34 attaches to the coupler 36 which, in turn, is coupled to the driven shaft 38 of the planetary system 40 of the motion converter 18 for rotating the same. As will be explained below, the planetary gear system 40 rotates the cam 42 and via the follower (see FIG. 3), which, in turn, translate the drum 46 and shaft 48 to impart reciprocal motion. The file assembly 20 includes the file 50 having an angular shaft 52, a blade 54 and tang 56. Tang 56 includes hole 58 (see FIG. 5) that cooperates with a complementary threaded hole 60 formed in the bifurcated end portion 62 (see FIG. 3) and with a suitable bolt 62 (not shown) fitted into hole 58 is threaded to hole 60 connects the file 50 to drum 46 for imparting reciprocating the file. As is obvious, the casing is split into two halves to gain access to the connection between the file assembly and the dome of the reciprocal converting mechanism.

It is typical in this type of these types of instruments to provide irrigation to the surgical site. To this end, the casing 12 includes port 42 and the lubricant transmittal tube 44 that is connected to the lumen 46 formed in the file assembly 20.

The next portion of this application will describe the inventive cam/drum configuration of the motion converter 18. The stub shaft 66 is suitably connected to the drive shaft 34 of motor 16 and carries pinion gear at the distal end thereof (The connection may equally be made by a direct connection without the use of a stub shaft). Pinion gear 68, in turn, meshes with each of the planetary gears 70, (three in number) which, in turn, meshes with the fixed ring gear 72. Ring gear 72 is fixed to the cam outer casing 73 via the dowel pin 75 disposed in the slot 77 formed in the flange 79. (The ring gear can be made integral with the cam outer casing). As is apparent from FIG. 3, each of the planetary gears 70 are rotary supported to stub shaft 74 which is suitably pinned to platen 76. Platen 76 is a portion of the rotating cam 78 which is rotated by the spinning planetary gears 70. Cam 69 includes the main body 71 that has formed therein the cam slot 80 that is designed to produce reciprocal motion as will be apparent from the following description. Follower 44 fitted into the cam slot 80 is pinned via pin 86 to drum 88. As noted, and in accordance with this invention, a single cam follower is all that is necessary to drive drum 88. Drum 88 comprises the hollow sleeve 90 (see FIG. 4) having the aperture 92 formed on the peripheral side thereof. The follower 44 consists of stub shaft 94 locks roller 96 to the hollow sleeve 90 via the recess 98. A washer 100 may be used to assure that the roller has sufficient spacing so that its rolling around shaft 94 is not impaired. In accordance with this invention, two (2) thrust pins 102 and 104 fit into annular groove 106 formed in the cam. The thrust pins 102 and 104 are grounded to the cam casing 108 and serve to absorb the thrust loads so as to allow the efficient operation of the surgical file.

In operation, the motor drives shaft 66 and pinion gear which, in turn, meshes with the three (3) planetary gears 70 which, in turn, meshes with the fixed ring gear 72. This reaction of all of the above mentioned gears rotates the cam 69 via the platen 76. The platen 76 which is integral with the cam 69, as a consequence, is rotated. This motion, in turn, is converted to reciprocal motion via the follower 44 that drives the drum in a reciprocal motion. Obviously, this motion is translated to the surgical file by the connection described above.

Also, in accordance with this invention the surgical file is unique as will be described in detail herein below. As mentioned above the file assembly comprises a longitudinally extending outer tube 112 that has formed thereon at the distal end a flat or planar shaped shield and guide member 115. A longitudinally extending solid rod 114 is tightly fitted into tube 112 formed with the "infinity shaped" slot 116 and a pair of lumens 46 and 47. (See FIG. 2A) And a generally longitudinally extending file 50 that fits into the infinity slot 116 and extends beyond the distal end of the solid rod 114 wherein the blade is complimentary dimensioned to the guide/shield and portions of the lower surface thereof are contiguous to portions of the upper surface of the guide/shield and in sliding relationship in the longitudinal direction. In its preferred embodiment, the elements in the surgical file assembly are bent 30 degrees adjacent to the proximal end and at the same angle adjacent to the distal end. Obviously, the particular shape and dimensions of the elements in the surgical file assembly will be predicated on its particular use.

As shown in FIGS. 6-8, the cutting surface of the blade 54 of file 50 consists of a plurality of radial projecting ring-like elements or micro holes 120 that serve as cutting edges 122. As mentioned earlier, the particular file head is not a concern of this invention. However, of importance is the shape of the guide/shield 115 and its relationship to the file head. Formed on shield 115 is the elongated dimple 124 extending longitudinally along the central portion of shield 115. The dimple includes the apex 126 and the straight slopes 128 and 130 extending from the top portion along either sides there of. This particular configuration defines a rail that centers the file and keeps its motion in a linear straight line which obviously, is important for the delicate types of precision operations to which the surgical file instrument is used. The lower portions 119 and 121 of the shield 115 extend radially toward the outer edges of blade 54 of the file 50 and are bent slightly upwardly to be in contiguous contact with the side edges of blade 54 of the file 50. As is apparent from the foregoing the guide/shield provides an efficient support for the blade 54 of the file 50 while assuring that the tissue or body parts adjacent to the operation site are not bruised or injured.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A surgical file instrument comprising:
   a surgical file having a shaft with a blade extending from one end thereof and a tang extending from the other end thereof, said surgical file having a relatively flat main body and said main body having an upper cutting surface and an underneath smooth surface;
   an elongated body extending into an outer tube casing, the elongated body having an infinity-shaped slot sized and configured to receive the shaft of the surgical file; and
   a guide/shield coupled to the distal end of the outer tube casing and disposed in parallel relationship with said blade and dimensioned to the same width of said blade, said guide/shield having a relatively planar main body.

2. The surgical file instrument of claim 1, wherein the side edges of said planar main body of the guide/shield extend longitudinally and are bent in an upward direction to bear against said underneath smooth surface of the surgical file.

3. The surgical file instrument of claim 1, further including:
   a dimple centrally formed in a longitudinal direction on said planar main body of the guide/shield and bearing against said underneath smooth surface of the surgical file along the longitudinal axis for holding said surgical file in a continuous straight line, said dimple including an apex bearing against said underneath smooth surface,
   side walls extending from either side of said apex along a straight line and to said planar main body of said guide/shield.

4. The surgical file instrument of claim 1, wherein the infinity-shaped slot of the elongated body includes an apex extending into an opening defined by the slot.

5. The surgical file instrument of claim 4, wherein the apex bears against the shaft of the surgical file.

6. The surgical file instrument of claim 1, wherein the guide/shield is formed on the outer tube casing.

7. The surgical file instrument of claim 1, wherein the elongated body has a lumen extending therethrough.

8. A surgical file instrument including:
   a surgical file assembly including:
      an outer tube casing;
      a rod insert extending into the outer tube casing, the rod insert having a slot extending therethrough; and
      a surgical file having a shaft extending through the slot included in the rod insert, the surgical file having a blade extending from one end of the shaft and a tang extending from the opposite end of the shaft, the blade having a smooth underneath surface, a distal end of the surgical file extending beyond a distal end of the rod insert and the tang extending beyond the rod insert on the other end;
      a flattened portion of said outer tube casing on a distal end defining a guide/shield for the blade;
   a battery operated motor for generating rotary motion;
   a motion converter including a planetary gear system rotary connected to said motor;
   a cam with a cam slot operatively connected to said planetary gear system;
   a drum disposed adjacent to said cam;
   a follower operatively connected to said slot for imparting reciprocal motion to said drum; and
   a connector on said drum connected to said tang for imparting reciprocal motion to said surgical file;
   whereby said dimple maintains said blade in line and free from wobbling when in the reciprocating condition.

9. The surgical file instrument of claim 8, wherein the side edges of said flatten portion are faired in an upward direction and engaging said underneath smooth surface.

10. The surgical file instrument of claim 9, including a casing for said planetary gear system,
    a pair of pins extending from casing and into an annular slot formed on said cam for absorbing thrust loads in said planetary gear system.

11. The surgical file instrument of claim 8, wherein the slot of the rod insert defines an infinity-shaped channel.

12. The surgical file instrument of claim 8, wherein the slot of the rod insert includes an apex extending into an opening defined by the slot.

13. The surgical file instrument of claim 12, wherein the apex bears against the shaft of the surgical file.

14. The surgical file instrument of claim 8, wherein the rod insert includes a pair of lumens extending therethrough.

15. The surgical file instrument of claim 14, wherein at least one of the pair of lumens is coupled to a lubricant transmittal tube.

16. The surgical file instrument of claim 8, wherein the rod insert is a solid plastic tube.

17. The surgical file instrument of claim 8, wherein the blade of the surgical file extends from the shaft of the surgical file at an angle of at least 30 degrees.

18. The surgical file instrument of claim 8, wherein the blade of the surgical file extends from the shaft of the surgical file at an angle less than 30 degrees.

19. The surgical file instrument of claim 8, wherein the flattened portion includes an longitudinally extending dimple that guides motion of the surgical file in a linear straight line.

* * * * *